United States Patent [19]

Graupe et al.

[11] Patent Number: 5,070,873
[45] Date of Patent: Dec. 10, 1991

[54] METHOD OF AND APPARATUS FOR ELECTRICALLY STIMULATING QUADRICEPS MUSCLES OF AN UPPER MOTOR UNIT PARAPLEGIC

[75] Inventors: Daniel Graupe, Highland Park; Stavros Basseas, Park Ridge, both of Ill.

[73] Assignee: Sigmedics, Inc., Northfield, Ill.

[21] Appl. No.: 14,389

[22] Filed: Feb. 13, 1987

[51] Int. Cl.$^5$ ............................................. A61N 1/00
[52] U.S. Cl. ............................................. 128/423 W
[58] Field of Search ...................... 128/423 W; 272/70

[56] References Cited

U.S. PATENT DOCUMENTS 4,582,049  4/1986  Ylvisaker .................. 128/423 W
4,697,808  10/1987  Larson et al. .................. 272/70

OTHER PUBLICATIONS

*Electromyographic Control of Functional Electrical Stimulation in Selected Patients*, by Graupe et al., Orthopedics, Jul. 1984, vol. 7, No. 7, pp. 1134–1138.
*EMG Response to Electrical Stimulation*, Etc., The Journal of Orthopaedic Surgical Techniques, vol. 2, No. 1, Mar. 1986, p. 61.

Primary Examiner—William H. Grieb
Attorney, Agent, or Firm—Sandler, Greenblum & Bernstein

[57] ABSTRACT

Muscle fatigue of an electrically stimulated quadriceps muscle of an upper motor neuron paraplegic is detected and compensated for by monitoring the myoelectric (EMG) signal produced by the stimulated muscle and controlling one or more of the following parameters of the electrical stimulation (ES) signal; its pulse repetition rate, its amplitude, and its pulse width.

29 Claims, 2 Drawing Sheets

FIG.2
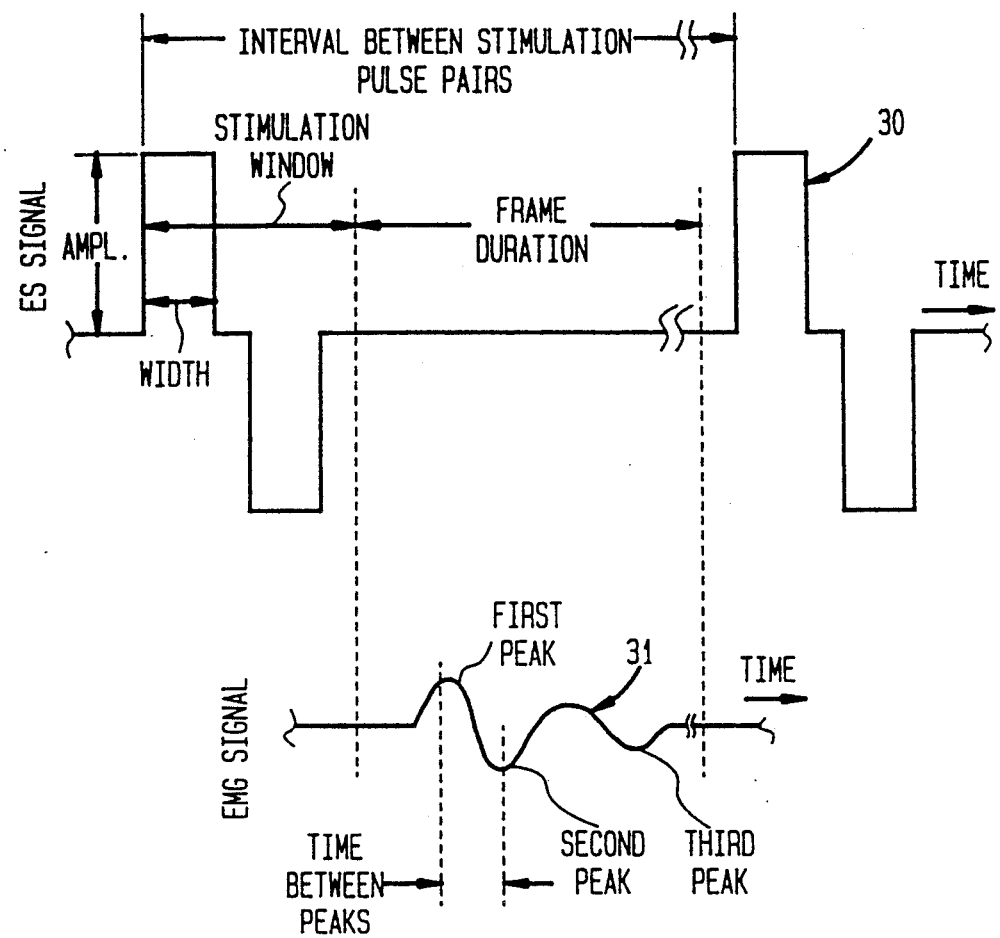
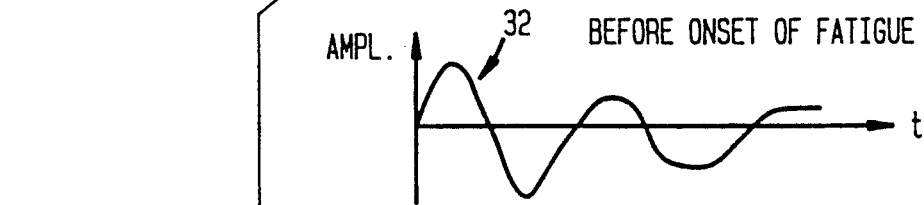
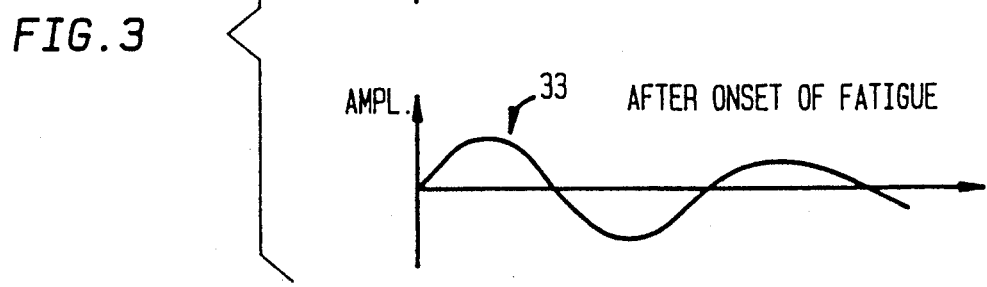
FIG.3

METHOD OF AND APPARATUS FOR ELECTRICALLY STIMULATING QUADRICEPS MUSCLES OF AN UPPER MOTOR UNIT PARAPLEGIC

DESCRIPTION

1. Technical Field

This invention relates to a method of and apparatus for electrically stimulating quadriceps muscles of an upper motor unit paraplegic.

2. Background

Certain upper motor neuron paraplegics have been able to stand and even walk by electrically stimulating their leg muscles. Conventionally, transcutaneous, surface electrodes, or needle electrodes, are applied to the quadriceps muscles of each leg of a paraplegic, and stimulating electrical signals are applied to the electrodes to provide muscle stimuli that effect execution by the paraplegic of standup, stepping, and sitting down functions.

While this description makes reference to muscle stimuli, the understanding should be that a muscle is a combination of neural motor units (NMU's) and muscle fibers. A quadriceps muscle thus is constituted by hundreds of NMU's, and thousands of fibers. What are electrically stimulated are actually NMU's; and, in response, the muscle fibers contract. In a healthy person, electrical stimulation of NMU's is achieved via the spinal cord; in a paraplegic, electrical stimulation occurs via electrodes applied to the paraplegic. The physical contraction of muscle fibers in response to stimulation of the associated NMU's causes the fibers to produce electro-myographic (EMG) signals. Thus, reference to stimulation of quadriceps muscles in this application is a short-hand way of referring to electrical stimulation of NMU's of the quadriceps muscles which, in turn, causes, or may cause, contractions of the muscle fibers associated with the MNU's.

Patients with spinal cord lesions located between T-8 and T-12 (dorsal) levels of the spinal cord may be able to walk under electrical stimulation of their quadriceps muscles with the help of a conventional walker because such patients usually have natural pelvic control. Once their quadriceps muscles are contracted under electrical stimulation, these patients can continue to walk by maintaining continuous quadriceps contractions. Experience shows that when muscle fatigue sets in, a given level of stimulation that creates muscle contractions adequate to permit a patient to stand for a certain duration of time, e.g., for a few minutes, is no longer adequate to maintain this function. That is to say, in order to maintain the patient in a standing position in the face of muscle fatigue, manual intercession is required to increase the stimulation level. The same situation applies after the patient has taken a number of steps.

The need to manually intercede in the stimulation process is highly undesirable because it interferes with the concentration of a patient during a standing or walking function is therefore an object of the present invention to provide a new and improved method of and apparatus for electrically stimulating quadriceps muscles of a paraplegic wherein the need is eliminated for manually adjusting the electrical stimulation level to compensate for muscle fatigue.

DISCLOSURE OF INVENTION

The present invention provides self adjusting apparatus for applying electrical stimulation (ES) to the MNU's of the sets of quadriceps muscles of an upper motor unit paraplegic. The apparatus according to the invention has a first channel comprising a controllable stimulation generator for generating an ES signal in the form of a train of pulses. In addition, the apparatus includes ES electrode means connected to the output of the stimulation generator for applying the ES signal to one set of quadriceps muscles of a patient thereby stimulating the same. The invention also includes EMG electrode means adapted to be connected to the stimulated muscle for picking up EMG signals produced by the stimulated muscle in response to its stimulation, and control means responsive to the EMG signals for controlling the stimulation generator by controlling one or more of the following ES parameters of the ES signal: the pulse repetition rate, the amplitude, and the pulse width of the train of pulses produced by the stimulation generator.

Preferably, one electrode means constitutes both the ES electrode means and the EMG electrode means. In this way, a single set of electrodes is provided for applying the stimulation signal to the quadriceps muscles as well as picking up the EMG signal produced by the stimulated muscles. In the preferred embodiment, the control means comprises means for separating the EMG signals from the ES signals and producing a separated EMG signal, means for processing the separated EMG signal to produce an EMG parameter representative of the separated EMG signal, a comparator responsive to EMG parameters produced at different times for producing a control signal when a later EMG parameter has a value less than a predetermined percentage of an earlier EMG parameter.

The invention also includes ES parameter means responsive to the control signal produced by the comparator for establishing an ES parameter of the ES signal. With this arrangement, a reference EMG parameter is established at, for example, the beginning of a function, such as standing or walking, so that a comparison can be made at a later time with this reference as the patient continues the function. As muscle fatigue sets in, the EMG parameter produced in response to the ES signal will be indicative of muscle fatigue when the EMG parameter decreases below a threshold thereby producing a control signal which increases the output level of the stimulation generator until the current EMG parameter matches the reference. In this manner, no manual intercession is required by a patient in order to maintain a function.

BRIEF DESCRIPTION OF DRAWINGS

An embodiment of the present invention is illustrated in the accompanying drawings wherein:

FIG. 2 is an idealized representation of a typical ES stimulation signal applied to a set of quadriceps muscles, and the EMG signal produced by the stimulated muscles, showing the temporal relationship between the signals; and FIG. 3 is an idealized representation of an EMG signal produced by a muscle before fatigue has set in, and at the onset of fatigue, for the purpose of comparing the two signals.

DETAILED DESCRIPTION

Figure 1:
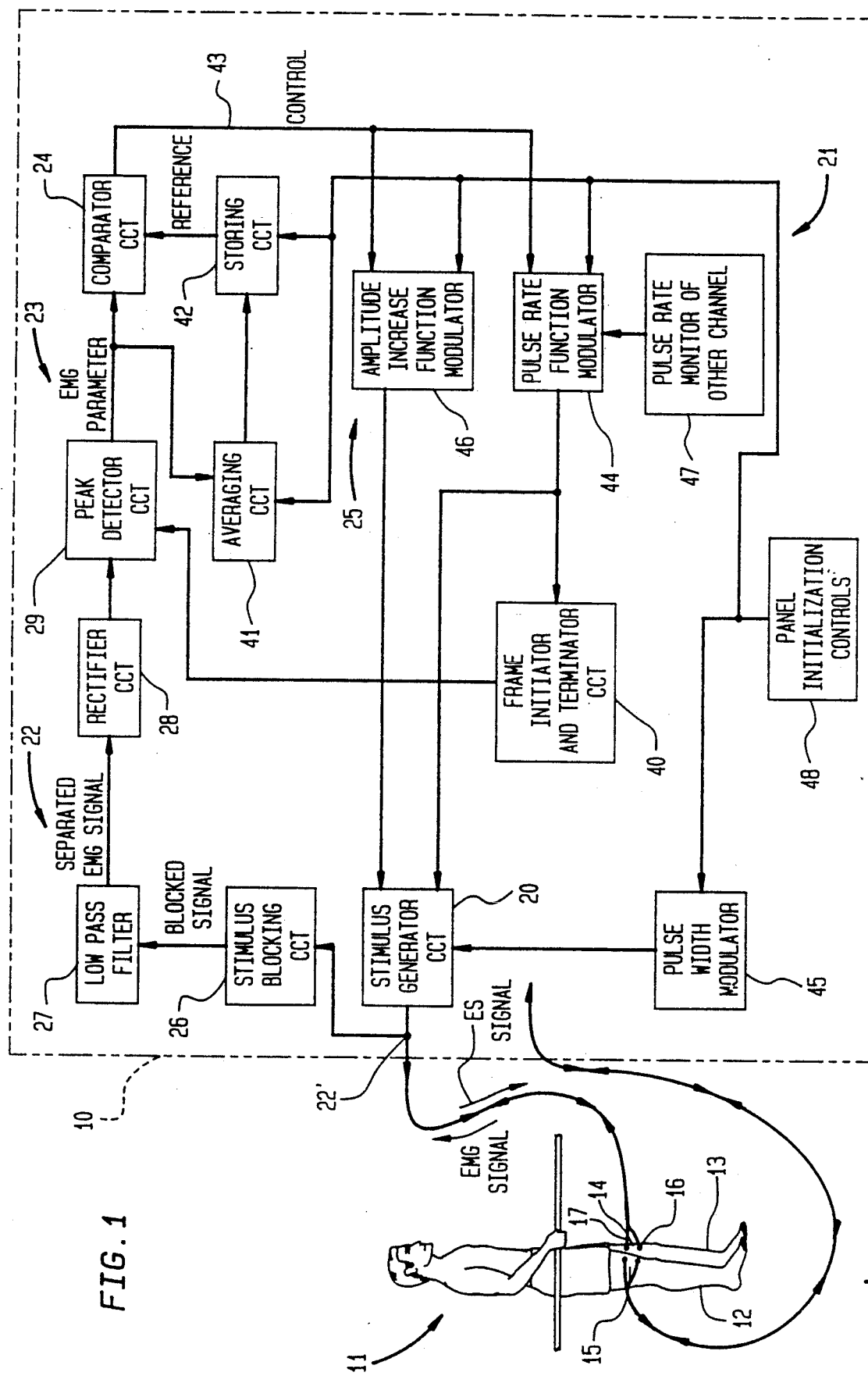
FIG. 1 represents a schematic block diagram of apparatus according to the present invention.

Referring now to the drawings, reference numeral 10 designates apparatus according to the present invention for electrically stimulating quadriceps muscles of an upper motor neuron paraplegic indicated by reference numeral 11. As indicated previously, muscle is considered to constitute both neural motor units of that muscle, and its muscle fiber. Each leg 12 and 13 of paraplegic 11 contains a set of quadriceps muscles in the region indicated generally at 14 and 15 in the upper thighs of the patient. In a conventional manner, transcutaneous surface electrodes, or needle electrodes, shown generally by reference numeral 16, are applied to each set of quadriceps muscles of patient 11. This provides a channel of stimulation for each leg; and FIG. 1 shows details of one of the two channels. Actually, a channel like that shown at 10 in FIG. 1 is also applied to a set of electrodes associated with the other leg of the patient.

The channel shown by reference numeral 10 comprises controllable stimulation generator 20 for generating an electrical stimulation (ES) signal in the form of a train of pulses. Such pulses may be bipolar, or unipolar, with a pulse repetition rate, amplitude and pulse width selected to provide such electrical stimulation of the quadriceps muscles of a patient as to achieve sufficient muscle contractions that allow a patient to perform a particular function, such as to stand or to continue standing, as shown in FIG. 1. Typical bipolar pulses are shown in FIG. 2 to which reference is now made.

Reference numeral 30 in FIG. 2 designates, in idealized form, a typical ES signal having bipolar pulses. Typically, the pulse repetition rate would be about 25 pulses per second so that, typically, the interval between stimulation pulse pairs is about 40 milliseconds (msec). Typically the pulse width is about 150 microseconds (usec), and the amplitude is about 40 millivolts (mvolts). Thus, an ES signal can be specified by its parameters of pulse repetition rate, amplitude, and pulse width.

Typically, pulse pairs are formed by a positive going pulse followed by a negative going pulse, although the converse can also be utilized. In either case, the second occurring one of a pulse pair follows the first occurring one by an interval that may vary from between zero to about 50 usec.

Apparatus 10 (FIG. 1) also includes ES electrode means 16, 17 connected in parallel to the output of generator 20 for applying the ES signal to one set of quadriceps muscles of patient 11 thereby stimulating such muscles. As is well known, a stimulated muscle produces myoelectric (EMG) signals in response to the stimulation process; and, to detect these signals, electrodes 16 and 17 are used. Alternatively, separate EMG electrodes may be provided. However, the advantage of using one electrode means to constitute both the ES electrode and the EMG electrode is obvious.

Reference numeral 31 applied to the lower curve of FIG. 2 represents a typical EMG signal that would be produced by an ES signal of the form shown at the top of FIG. 2. That is to say, the amplitude of the EMG signal is two to three orders of magnitude longer than the ES signal. Furthermore, its duration is at least two orders of magnitude smaller than the period of the ES signal. Thus, an EMG signal appears in time subsistent to a pulse pair and constitutes a series of diminishing alternating voltages inducted by curve 31 of FIG. 2. Where the period of the ES signal is around 40 sec, the EMG signal produced by a pulse pair stimulation of a muscle would appear shortly after the termination of an excitation pulse pair, and would decay to zero before the beginning of the next excitation pulse pair. Parameters of an EMG signal produced in response to a bipolar ES signal are the relative amplitudes of the various peaks of the EMG signal, the time intervals between the peaks, as well as the period of the EMG signal.

Experimentally, it has been found that EMG signals produced by stimulated muscle begin to change at the onset of fatigue. This is illustrated in FIG. 3 wherein curve 32 is representative of an EMG signal produced before the onset of fatigue. Subsequently, the EMG signal will have the form shown at 33 wherein the amplitude of the signal is less than the amplitude of signal 32, and the time period between successive peaks of the signal is greater than before. Thus, incipient muscle fatigue can be detected in terms of the changes in the parameters of the EMG signal by monitoring, changes in the value of the first peak of the EMG signal, or changes in the relationship of subsequent peaks from the first peak.

A purpose of the present invention, and a function of the electronics of apparatus 10, is to separate the EMG signal produced by a stimulated muscle from the stimulating ES signal, to detect incipient muscle fatigue by detecting changes in the parameters representative of the EMG signal, and to change the parameters of the ES signal in response to changes in the parameters of the EMG signal such that the muscle is stimulated to a greater degree thereby returning the EMG signal to the levels before the onset of fatigue. To this end, apparatus 10 also includes control means 21 responsive to one or more parameters of the EMG signal for controlling stimulation generator 20 by controlling one or more of the following ES parameters of the ES signal: its pulse repetition rate, its amplitude, and the pulse width.

As shown in FIG. 1, the signal appearing at node 22 at the output of stimulation generator 20 contains an outgoing ES signal produced by stimulation generator 20 and an incoming EMG signal produced by the muscle stimulated by the ES pulses. As shown in FIG. 2, the outgoing ES signals and the incoming EMG signals are time-multiplexed; and one function of control means 21 is to separate the EMG signal from the ES signal in order to permit processing of the EMG signals so that they can be used to control the parameters of the ES signal. Thus, control means 21 also includes means 22 for separating EMG signal from the ES signal and producing a separated EMG signal, means 23 for processing a separated EMG signal to produce an EMG parameter representative thereof, comparator 24 responsive to EMG parameters produced at different times for producing a control signal when a later EMG parameter has a value less than a predetermined percentage of an earlier EMG parameter, and ES parameter means 25 responsive to the control signal for establishing the ES parameters used to control generator 20.

Circuit 22 for separating EMG signals from ES signals comprises blocking circuit 26 connected to electrodes 16 and 27 through node 22, and serves to block portions of the ES signal for producing what is termed a blocked signal. Means 22 also includes low pass filter 27 responsive to the blocked signals produced by blocking circuit 26 for filtering remaining portions of the ES signal and producing what is termed a separated EMG signal.

Blocking circuit 26 is a clipping circuit that clips the applied signals at a predetermined level thereby blocking any input signal whose amplitude exceeds the threshold of the blocking circuit. Consequently, the blocked signal produced by blocking circuit 26 is a signal whose level is less than the threshold of the blocking circuit. Recalling that EMG signals are several orders of magnitude smaller than ES signals, the threshold of blocking circuit 26 is set to a value of from one to three orders of magnitude less than the output level of generator 20. Moreover, the duration of the stimulus is at least two orders of magnitude smaller than the duration of the resultant EMG signal. With these parameters in minds blocking circuit 26 will be active less than 5-10% of the time.

Alternatively, or in addition, blocking circuit 26 can be operated as a gated blocking circuit. In such case, it would be made active only during the time that an EMG signal is expected, i.e., between successive pulse pairs of the ES signal.

The so called blocked signal produced by blocking circuit 26 is filtered by low pass filter 27 such that the output of the filter, namely the so called separated EMG signal, contains almost no remnant of the ES signal. The separated EMG signal at the output of filter 27 is applied to rectifier circuit 28 which converts all negative voltage values of the EMG signal to positive values before applying them to peak detector circuit 29. In the preferred embodiment of the invention, only the first peak (see FIG. 2) of an EMG signal is detected and measured, the output of circuit 29 being a signal representative of this peak. However, the second and subsequent peaks may also be detected, and signals representative of their amplitudes can be outputted from a peak detector circuit in a known manner. In addition, or alternatively, the time intervals between successive peaks may be detected and saved for later processing.

As explained below, the peak values of the EMG signals produced as a consequence of initiation of stimulation, i.e., initial operation of generator 20, are accumulated over typically ten frames Of excitation and averaged to establish a reference or baseline against which later occurring peak values of EMG signals can be compared In this way, a reduction in peak value of a later occurring EMG signal, as compared to the reference, will establish incipient muscle fatigue.

Frame initiator and terminator circuit 40 is effective to establish the start and duration of what is termed a frame within the period of the pulses that constitute the ES signal. That is to say, circuit 40 causes a frame to start a predetermined time subsequent to the termination of a bipolar pulse pair of the ES signal. During typically the first ten frames following initiation of operation of circuit 20, the output of detector 29 is applied to averaging circuit 41 which functions in a known manner to average the peak values supplied to circuit 41 by detector 29. Thus, after typically ten frames of operation (which occur within about four seconds following initial turn-on of apparatus 10), circuit 41 will produce an output that is a representation of the average, initial first peak values of the EMG signals produced by the stimulated muscle. Such representation, preferably a percentage of the average first peak values, is stored in storing circuit 42.

The output of detector 29 is also applied to comparator 24 so that each first peak of an EMG signal is compared with the average of the first peak values of the initial EMG signals. When the current first peak value of an EMG signal is less than the average of the first peak values stored in circuit 42 by a predetermined percentage, comparator 24 generates a control signal that appears in line 43.

The parameters of the ES signal produced by generator 20, namely its pulse repetition gate, its pulse width, its amplitude, and its period or duty cycle, are established by pulse rate modulator 44, pulse width modulator 45, and amplitude modulator 46. The operation of each of modulator circuits 44, 45, and 46 is controlled by the control signal in line 43. That is to say, the operation of each of circuits 44, 45, and 46 is responsive to the output of comparator 24. These circuits are designed to respond to a control signal in line 43 in a programmed sense: i.e., modulator 45 responds by causing the pulse width of the ES signal produced by generator 20 to increase in a predetermined step; modulator 44 responds by causing the pulse rate of the ES signal produced by generator 20 to increase in a predetermined step; and modulator 46 responds by causing the amplitude of the pulses of the ES signal to increase in a predetermined step.

Preferably, the rate at which stimulation is applied to the other set of quadriceps muscles of a patient by the second channel (not shown) is monitored and used to further modify the operation of apparatus 10 which, it will be recalled, is but one of two channels used with a patient. To this end, monitor 47 is a part of apparatus 10 and is responsive to the pulse repetition rate of the other channel for modifying the pulse repetition rate of apparatus 10 by operating on modulator 44 in parallel with a control signal in line 43. In this manner, the firing of generator 20 of apparatus 10 is made complimentary to the firing of a comparable generator in the other channel. That is to say, when the pulse repetition rate in one channel increases, as a consequence of fatigue of the muscle stimulated by the one channel, the pulse repetition rate in the other channel decreases.

Pulse width modulator 44 is programmed to gradually increase/decrease the pulse width of the ES signal during initialization/termination of a stimulation cycle for effecting a smooth contraction/relaxation of the stimulated muscle. Finally, initialization circuit 48 establishes the initial conditions for each of modulators 44, 45 and 46, and serves to clear and reset circuits 41 and 42.

In operation, circuit 48 is activated to initialize the components of apparatus 10 in accordance with known medical procedures. Electrodes 16, 17 are applied in a known manner to the quadriceps muscles in one leg of a patient, and connected to node 22 of apparatus 10. Corresponding electrodes are also applied to the quadriceps muscles in the other leg and connected to another channel line that shown in FIG. 1. The apparatus is now ready for operation which begins when generator 20 is activated.

Upon activation of generator 20, an ES signal in the form of a pulse train like that designated by reference numeral 30 is applied to the quadriceps muscles to which electrodes 16, 17 are applied. The level of stimulation is effectively the integral of the absolute value of the ES signal over time evaluated over a certain time interval, typically one second. Thus, the stimulation level is a function of the parameters of the ES signal, namely its pulse repetition rate, its pulse amplitude, and/or the its width.

Circuit 26 clips the signal appearing at node thus blocking most of the much larger amplitude ES signal and producing a blocked signal which is applied to filter 27 that eliminates almost all remnant of the ES signal allowing rectifier circuit 28 to produce a rectified version of each EMG signal produced by the stimulated muscle in response to the application of a bipolar pulse pair. The first peak of this rectified signal is applied to both comparator 24 and circuit 41; and the cycle is repeated for typically ten pulse pairs produced by generator 20. These ten first peak values are accumulated and averaged in circuit 41 which produces a representation of the average on the first ten peak values and stores a predetermined percentage of such average in circuit 42. First peak values of subsequence EMG signals produced by subsequent pulse pairs of the ES signal are compared by circuit 42 with the reference stored in circuit 42. If the subsequent first peak value drops below the threshold established by circuit 42, comparator 43 produces a control signal in line 43. Modulators 44, 45, and 46 are responsive to such a control signal for increasing the pulse repetition rate, the pulse amplitude, and the pulse width of the ES signal in fixed steps to thereby increase the level of stimulation of the muscle to which electrodes 16, 17 are applied. By increasing its stimulation level, the muscle will respond by increasing the level of the EMG signal; and as a result, the next first peak of the EMG signal, will exceed the reference thereby compensating for the effect of muscle fatigue.

In practice, it has been found that while a patient is standing, and the both sets of quadriceps muscles are stimulated to produce the required leg and/or knee extensions required to maintain the patient in a standing position, the pulse repetition rate in one channel may be well below 25 pulse per second, while at the same time, the pulse repetition rate in the other channel may be at about 25 pulses per second, the rates alternating as the patient continues to stand. Sometimes, the pulse repetition rate in both channels is reduced simultaneously upon detection of fatigue, er re-reduced at a later detection of muscle fatigue. In other cases, the pulse repetition rate is changed in each channel simultaneously.

While a bipolar pulse pair is described in detail above, the present invention also contemplates using monophasic stimuli, i.e., stimuli in the form of a single (positive or negative) pulse at each pulse interval. In such case, the time-wise first occurring peak in the EMG signal produced by the muscle stimulated by the single pulse is actually a stimulus artifact caused by the leakage effect of the stimulation pulse. It carries no information on the response-EMG relative to muscle fatigue. Consequently, the circuitry of processing means 23 is configured to ignore the artifact peak in each EMG signal produced as a consequence of a monophasic pulse, and to respond to only the legitimate first peak pulse in the EMG signal. Thus, when the term first peak pulse is used, it means the first legitimate peak pulse in an EMG signal.

The advantages and improved results achieved by the method and apparatus of the present invention are apparent from the foregoing description of the preferred embodiment of the invention. Various changes and modifications may be made without departing from the spirit and scope of the invention as described in the claims that follow.

We claim:

1. Self adjusting apparatus for the electrical stimulation of neural motor units (NMU's) of the sets of quadriceps muscles of an upper motor neuron paraplegic, said apparatus having a first channel comprising:

(a) a controllable stimulation generator for generating an electrical stimulation (ES) signal in the form of a train of pulses;
   (b) ES electrode means connected to the output of said stimulation generator for applying said ES signal to the MNU's of one set of quadriceps muscles thereby stimulating the same;
   (c) EMG electrode means adapted to be connected to the stimulated muscles for picking up myoelectric (EMG) signals produced thereby in response to the ES signal; and
   (d) control means responsive to said EMG signals for controlling said stimulation generator by controlling one or more of the following ES parameters of said ES signal: pulse repetition rate, amplitude, and pulse width of the train of pulse produced by said stimulation generator.

2. Self adjusting apparatus according to claim 1 wherein one electrode means constitutes both said ES electrode means and the EMG electrode means.

3. Self adjusting apparatus according to claim 2 wherein said control means comprises:

(a) means for separating EMG signals from said ES signals and producing a separated EMG signal;
   (b) means for processing a separated EMG signal to produce an EMG parameter representative thereof;
   (c) comparator means responsive to EMG parameters produced at different times for producing a control signal when a later EMG parameter has a value less than a predetermined percentage of an earlier EMG parameter; and
   (d) ES parameter means responsive to said control signal for establishing said ES parameters.

4. Self adjusting apparatus according to claim 3 wherein said means for separating includes:

(a) blocking means connected to said same electrode means and responsive to the applied ES signal and the pickoff EMG signal for blocking portions of said ES signal and producing blocked signals; and
   (b) filter means responsive to said blocked signals for filtering remaining portions of said ES signal and producing said separated EMG signal.

5. Self adjusting apparatus according to claim 4 wherein said blocking means clips the applied signals at a predetermined level whereby said blocked signal consists of only of signals of less than said predetermined level.

6. Self adjusting apparatus according to claim 5 wherein said filter means is low pass filter for producing said separated EMG signal by eliminating remnants of said ES signal in said blocked signal.

7. Self adjusting apparatus according to claim 3 wherein said means for processing includes detector means for detecting peaks in said separated EMG signal which occur within a time frame lying between successive pulses of said ES signal, each peak of a separated EMG signal being the EMG parameter representative thereof; and storage means for storing a reference representative of peaks produced during initial application of said ES signal to said muscle; and said comparator means is constructed and arranged to compare a current peak in said separated EMG signal with said reference.

8. Self adjusting apparatus according to claim 7 wherein said ES parameter means comprises a pulse rate modulator circuit for controlling the pulse repetition rate of said stimulation generator, said last mentioned modulation circuit being constructed and arranged to increase the pulse repetition rate by a predetermined amount in response to a control signal from said comparator means.

9. Self adjusting apparatus according to claim 8 wherein said means for processing includes frame control means responsive to the output of said pulse rate modulator circuit for establishing the limits of said time frames.

10. Self adjusting apparatus according to claim 3 wherein said ES parameter means comprises a pulse amplitude modulator circuit for controlling the amplitude of the pulses produced by said stimulation generator, said last mentioned modulator circuit being constructed and arranged to increase the amplitude of said ES signal by a predetermined amount in response to a control signal from said comparator means.

11. Self adjusting apparatus according to claim 3 wherein said ES parameter means comprises a pulse width modulator circuit for controlling the pulse width of the pulses produces by said stimulator generator, said last mentioned modulator circuit being constructed and arranged to increase the pulse width by a predetermined amount in response to a control signal from said comparator means.

12. Self adjusting apparatus according to claim 3 wherein said ES parameter means comprises:
 (a) a pulse rate modulator circuit for controlling the pulse repetition rate of said stimulation generator, said last mentioned modulator circuit being constructed and arranged to increase the pulse repetition rate by a predetermined amount in response to a control signal from the comparator means;
 (b) a pulse amplitude modulator circuit for controlling the amplitude of the pulses produced by said stimulation generator, said last mentioned modulator circuit being constructed and arranged to increase the amplitude of the pulses produced by said stimulation circuit by a predetermined amount in response to a control signal from said comparator means; and
 (c) a pulse width modulator circuit for controlling the pulse width of the pulses produced by said stimulation generator, said last mentioned modulator circuit being constructed and arranged to increase the pulse width by a predetermined amount in response to a control signal from said comparator means.

13. Self adjusting apparatus according to claim 8 including a pulse rate monitor for monitoring the pulse repetition rate of a second channel whose ES electrode means are applied to the NMU's of the other set of quadriceps muscles of said paraplegic, said monitor being constructed and arranged to cause said ES parameter control means to change the pulse repetition rate of said first channel complimentary to changes in the pulse repetition rate of said second channel.

14. Self adjusting apparatus according to claim 8 including a pulse width modulator for controlling the pulse width of the pulses of the ES signal, said pulse width modulator being constructed and arranged to increase the pulse width during initial stimulation, and to decrease the pulse width during termination of stimulation for effecting smooth contraction/relaxation of the muscle being stimulated.

15. Self adjusting apparatus according to claim 14 wherein said stimulation generator is constructed and arranged to produce monopolar pulses.

16. Self adjusting apparatus according to claim 1 wherein said stimulation generators is constructed and arranged to produce pairs of bipolar pulses.

17. Self adjusting apparatus according to claim 16 wherein the pulses of a pair have a width of 50-200 microseconds, and are separated by less than about 50 microseconds, and the pulse repetition rate is about 25 pulses per second.

18. Self adjusting apparatus according to claim 17 wherein a sequence of bipolar pulses is a positive pulse followed by a negative pulse.

19. Self adjusting apparatus according to claim 17 wherein a sequence of bipolar pulses is a negative pulse followed by a positive pulse.

20. Self adjusting apparatus according to claim 1 including a second channel like said first channel for electrically stimulating the NMU's of the other set of quadriceps muscles of said paraplegic, the maximum pulse repetition rate of the ES signal being about 25 pulses per second, and the minimum being much less than 25 pulse per second, the rate alternating between the channels in complimentary fashion.

21. Self adjusting apparatus according to claim 7 including switch means for selectively resetting said storage means and effecting storage of a new reference during a stimulation session.

22. Self adjusting apparatus according to claim 3 wherein said means for processing detects and stores successive peaks of said separated EMG signals which occur within a time frame lying between successive pulses of said ES signal, and also stores the time between said successive peaks, the amplitudes of said successive peaks, and said time periods therebetween being the EMG parameters representative of a separated EMG signal.

23. A method for electrically stimulating the NMU's of the sets of quadriceps muscles of an upper motor unit paraplegic comprising the steps of:
 (a) producing an electric stimulation (ES) signal in the form of the train of pulses;
 (b) applying said train of pulse to al least one set of quadriceps muscles;
 (c) monitoring myoelectric (EMG) signals produced by the set of stimulated muscles in response to the ES signals to produce an EMG parameter representative of the EMG signal; and
 (d) modulating the ES signal in accordance with said EMG parameter.

24. A method according to claim 23 wherein one or more of the following ES parameters of the ES signal is modulated: the pulse repetition rate, the amplitude, and the pulse width of the train of pulses that constitute the ES signal.

25. A method according to claim 24 wherein an ES signal is also applied to the other set of quadriceps muscles, and wherein the pulse repetition rate of the ES signal is modulated such that while the patient is standing, and while both sets of quadriceps muscles are stimulated to produce leg and/or knee extensions for standing, the pulse repetition rate applied to one set of quadriceps muscles is well below 25 pulses per second, whereas at the same time the pulse repetition rate applied to the other set of quadriceps muscles is about 25 pulses per second.

26. A method according to claim 24 wherein the pulse repetition rate of the ES signal is modulated by detecting peaks in the EMG signal within a time frame defined by successive pulses of said ES signal, storing a reference representative of peaks produced during initial application of said ES signal to said muscle, and comparing a current peak in said EMG signal with said reference for the purpose of determining when the current peak falls below a threshold indicative of the onset of muscle fatigue.

27. A method according to claim 23 wherein the EMG parameter includes one or more of the following: successive peaks in the EMG signal within the period between successive pulses of said ES signal, and time periods between such successive peaks; and said method includes storing the EMG parameters that results from initial stimulation to define a standard parameter, and comparing later occurring EMG parameters with the standard parameter, and modulating the ES signal in accordance with the results of the comparison step.

28. A method according to claim 25 wherein the pulse repetition rate of signals applied to each set of quadriceps muscles are simultaneously changed when muscle fatigue is detected.

29. A method according to claim 25 wherein changes in the pulse repetition rate of signals applied to each set of quadriceps muscles are simultaneously changed.

* * * * *